United States Patent [19]

Romer et al.

[11] Patent Number: 5,180,740
[45] Date of Patent: Jan. 19, 1993

[54] COMPOSITION AND USE OF DIMERCAPTO-SUBSTITUTED DINITRILES AS AN ANTIMICROBIAL

[75] Inventors: Duane R. Romer; R. Garth Pews, both of Midland, Mich.

[73] Assignee: The Dow Chemical Company, Midland, Mich.

[21] Appl. No.: 814,526

[22] Filed: Dec. 30, 1991

[51] Int. Cl.$^5$ ..................... A01N 47/48; C07C 331/12
[52] U.S. Cl. ........................................ 514/516; 558/11
[58] Field of Search ............................ 514/516; 558/11

[56] References Cited

U.S. PATENT DOCUMENTS

| | | | |
|---|---|---|---|
| 2,533,233 | 12/1950 | Edwards et al. | 260/465.8 |
| 3,449,388 | 6/1969 | Lewis et al. | 260/429.9 |
| 3,776,891 | 12/1973 | D'Amico | 260/79.5 B |
| 4,087,451 | 5/1978 | Merianos | 260/454 |
| 4,389,400 | 6/1983 | Ho | 424/248.52 |

OTHER PUBLICATIONS

*Derwent Publications*, 90-094576/13, Jipukomu KK, JP2045-460-A, Aug. 3, 1988.
*U.S. Patent Official Gazette*, (1951) Abstract of U.S. Pat. No. 2,539,910, to Johnson et al., issued Jun. 10, 1948, "Insecticidal Composition Comprising 1,4-Dithiocyanobutene-2".

*Derwent Publication*, 27750Y/16, Kumiai Chem Ind KK, JP 002559, Jul. 26, 1975.
*Chemical Abstracts*, vol. 107, p. 595, 107:32114j, "Alkaline-Earth Metal Compounds of 1,1-Dicyano-Ethylene-2,2-Dithiolate. III.", *Z. Naturforsch.,B:Anorg. Chem. Org. Chem* 1986, 41B(10), 1206-10.

*Primary Examiner*—Richard L. Raymond

[57] ABSTRACT

Dimercapto-substituted dinitriles are prepared which correspond to the formula:

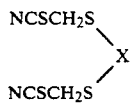

wherein X represents:

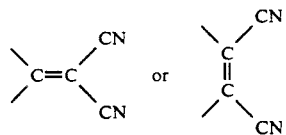

These compounds have been found to exhibit antimicrobial activity in industrial and commercial applications and compositions containing these compounds are so employed.

11 Claims, No Drawings

COMPOSITION AND USE OF DIMERCAPTO-SUBSTITUTED DINITRILES AS AN ANTIMICROBIAL

BACKGROUND OF THE INVENTION

This invention pertains to the use of dimercapto-substituted dinitrile compounds as antimicrobials agents.

U.S. Pat. No. 2,533,233 discloses the preparation of compounds of the formula:

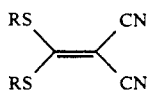

wherein R in an alkyl or aralkyl group. These compounds are disclosed as being useful as intermediates for the production of organic compounds of commercial utility. U.S. Pat. No. 3,776,891 discloses the preparation of compounds of the formula:

$(CN)_2C=C(S-A-NRR_1)_2$ wherein A represents a straight- or branched-chain alkylene of 2-4 carbon atoms and R and $R_1$ independently represent lower alkyl, aralkyl or cycloalkyl. These compounds are disclosed as being useful as accelerators for the vulcanization of rubber.

U.S. Pat. No. 4,087,451 discloses the preparation of compounds of the formula:

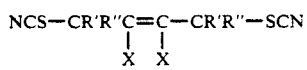

wherein X represents chlorine, bromine or iodine, and R' and R" may be the same or different and are selected from the group consisting of hydrogen and acyclic hydrocarbon monovalent radicals having 1-8 carbon atoms. These compounds are disclosed as being useful as antimicrobials.

U.S. Pat. No. 4,389,400 discloses the preparation of compounds of the formula:

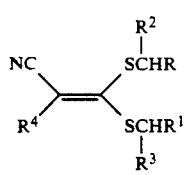

wherein X represents chlorine, bromine or iodine, and R' and R" may be the same or different and are selected from the group consisting of hydrogen and acyclic hydrocarbon monovalent radicals having 1-8 carbon atoms. These compounds are disclosed as being useful as antimicrobials.

The desirability of identifying or discovering new antimicrobial agents is widely recognized. New antimicrobial agents are desired for several reasons: these include, but are not limited to, responding to the problem created by the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves these problems by disclosing new compounds which may be employed as an antimicrobial.

SUMMARY OF THE INVENTION

The present invention is a compound corresponding to the formula:

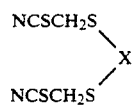

wherein X represents:

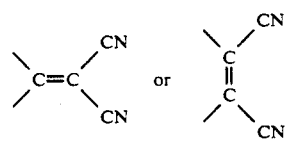

The present invention is also an antimicrobial composition comprising an inert diluent and an antimicrobially-effective amount of a compound corresponding to the formula:

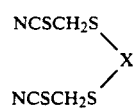

wherein X represents:

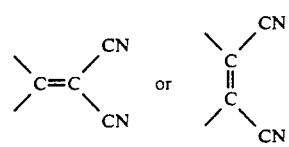

The present invention is also a method for inhibiting microorganisms in a microbial habitat comprising contacting said microbial habitat with an antimicrobially-effective amount of a compound corresponding to the formula:

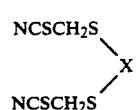

wherein X represents:

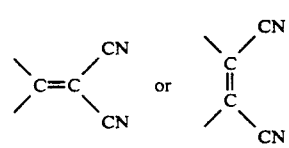

DETAILED DESCRIPTION OF THE INVENTION

The present invention is a compound corresponding to the formula:

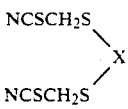

wherein X represents:

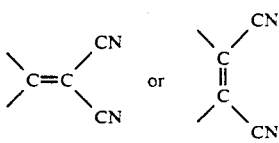

The bis(thiomethylthiocyanate)methylene)-propanedinitrile compound of the present invention, wherein X represents:

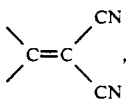

may be prepared by the reaction of chloromethylthiocyanate with di(sodiomercapto)methylenemalononitrile. The general reaction scheme for this reaction is as follows:

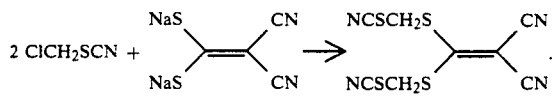

The use of di(sodiomercapto)methylenemalononitrile to prepare other compounds is known and is generally disclosed in U.S. Pat. Nos. 4,038,393: 4,075,204 and 4,075,205.

The Z-2,3-bis(thiomethylthiocyanate)-2-butenedinitrile compounds of the present invention, wherein X represents:

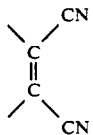

may be prepared by the reaction of chloromethyl-thiocyanate with disodium dimercaptomaleonitrile. The general reaction scheme for this reaction is as follows:

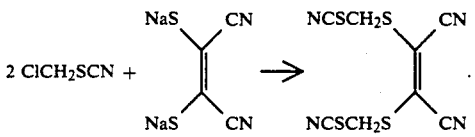

The use of disodium dimercaptomaleonitrile to prepare other compounds is known and is generally disclosed in U.S. Pat. Nos. 3,761,475: 4,172,133: 4,199,581 and 4,210,645.

In carrying out these reactions, the chloromethylthiocyanate and the di(sodiomercapto)methylenemalononitrile and/or disodium dimercaptomaleonitrile are typically mixed together in substantially 2 to 1 molar ratio amounts. Preferably, the chloromethylthiocyanate is added dropwise to a solution of the di(sodiomercapto)-methylenemalononitrile and/or disodium dimercapto-maleonitrile.

Other alkaline or alkali earth metal salts such as, for example, the dipotassium salts, of X-2,3-dimercapto-2-butenedinitrile and (dimercaptomethylene)propanedinitrile may also be substituted for the disodium salts in the reaction mixture.

Preferably, the reactions are carried out in an inert solvent such as dimethyl formamide, methanol, acetonitrile, acetone, or pyridine. Preferably, the reactions are carried out at 0° C. under an ambient pressure of inert gas. Subsequent to the addition of the appropriate reaction materials, the reaction mixture is allowed to stir at a temperature of between about 25° C. to about 60° C. for a period of between about 2 to about 24 hours in order to increase the reaction rate and promote extinction of the limiting reagent. Final work-up of the reaction mixture then provides the desired final product.

PREPARATION OF STARTING MATERIALS

The synthesis of chloromethylthiocyanate is straightforward and is described in the art, such as in Japanese Patents 62215561 and 62215562.

The synthesis of (sodiomercapto)methylenemalononitrile is straightforward and is described in the art, such as in A. Adams et al., *J. Chem Soc.*, 3061 (1959)

The synthesis of disodium dimercaptomaleonitrile is straightforward and is described in the art, such as in Muetterties, *Inorganic Synthesis*, Volume X, p. 11.

The following examples illustrate the present invention and the manner by which it can be practiced but, as such, should not be construed as limitations upon the overall scope of the same.

EXAMPLE 1

Preparation of Bis(thiomethylthiocyanate)-methylene)propanedinitrile

To a solution of (dimercaptomethylene)propanedinitrile-disodium salt (4.33 grams, 0.023 mol) in dimethyl formamide (40 mL) at 0° C. is added, dropwise, chloromethylthiocyanate (5.0 grams, 0.046 mol). The resulting solution is allowed to warm to room temperature and is stirred for 2 hours. The reaction mixture is poured into 150 mL of water, followed by extraction with three 50 mL portions of dichloromethane. The combined organic extracts are washed with water and brine followed by drying (with sodium sulfate) and concentration. Recrystallization of the residue from dichloromethane/hexanes gives (bis(thiomethylthiocyanate)methylene)-propanedinitrile as fine yellow needles.

The recovered material weighs 3.3 grams and has a melting point of 143° to 146° C. A calculated overall yield of 67 percent is achieved.

The structure identity is confirmed by proton nuclear magnetic resonance spectroscopy ($^1$H), carbon nuclear magnetic resonance spectroscopy (NMR), infrared spectroscopy (IR) and gas chromatography/mass spectrometry (GC/MS).

EXAMPLE 2

Preparation of Z-2,3-Bis(thiomethylthiocyanate)-2-Butenedinitrile

To a solution of Z-2,3-dimercapto-2-butenedinitrile-disodium salt, (4.3 grams, 0.023 mol) in dimethyl formamide (40 mL) at 0° C. is added dropwise, chloromethylthiocyanate (5.0 grams, 0.046 mol). The resulting solution is warmed to room temperature and is stirred for 2 hours. The reaction mixture is poured into 150 mL of water, followed by extraction with three 50 mL portions of dichloromethane. The combined organic extracts are washed with water, brine and dried (with sodium sulfate) and then concentrated. Recrystallization from dichloromethane/hexanes gives 2.62 grams (40 percent yield) of Z-2,3-bis(thiomethylthiocyanate)-2-butenedinitrile as tan colored prisms and has a melting point of 90° to 93° C.

ANTIMICROBIAL ACTIVITY

The compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, the two compounds disclosed herein are not necessarily active at the same concentrations or against the same microbial species. That is, there is some compound-to-compound variation in antimicrobial potency and spectrum of antimicrobial activity.

The present invention is also directed to a method for inhibiting microorganisms which comprises contacting said microorganisms or habitat thereof with an effective amount of the compound of this invention.

The antimicrobial compounds of this invention may be added directly to aqueous formulations susceptible to microbial growth, either undiluted or dissolved in inert diluents such as organic solvents such as glycols, alcohols, or acetone. They may also be added alone or in combination with other preservatives.

As used herein, the term "microorganism" is meant to refer to bacteria, fungi, viruses, algae, subviral agents and protozoa.

As used herein, the term "antimicrobially-effective amount" refers to that amount of one or a mixture of both the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular compound tested and microorganism treated Also, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

TABLE I

Identification of Compounds Used in Antimicrobial Activity Tests

| Compound No. | Chemical Identity |
|---|---|
| A | Bis(thiomethylthiocyanate)methylenepropanedinitrile |
| B | Z-2,3-bis(thiomethylthiocyanate)-2-butenedinitrile |

The minimum inhibitory concentration (MIC) for the compounds listed in Table I is determined for 9 bacteria, using nutrient agar, and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04 M solution of N-[tris-(hydroxymethyl)methyl]glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour-cultures of each of the bacteria are prepared by incubating the respective bacteria in tubes containing nutrient broth for 24 hours at 30° C. in a shaker. Dilutions of each of the 24 hour-cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC. test described above along with their respective American Type Culture Collection (ATCC) identification numbers.

In Tables III and IV, the MIC values of the compounds described in Table I as compared to the MIC of a standard commercial preservative (DOWICIL TM 75, a trademark of The Dow Chemical Company, with 1-(3-chloroallyl)-3,5,7-triaza-1-azoniaadamantane chloride as the active agent) are set forth for the nine bacteria organisms and six yeast/fungi organisms which are listed in Table II.

TABLE III

| | Minimum Inhibitory Concentrations for Test Compounds in Bacteria Species (in ppm) | | | | | | | | |
|---|---|---|---|---|---|---|---|---|---|
| | ORGANISMS | | | | | | | | |
| Compound | Bs | Ea | Ec | Kp | Pv | PRD | Pa | Sc | Sa |
| DOWICIL TM 75 | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| (A) | | | | | | | | | |
| pH 6.8 | 25 | 25 | <10 | <10 | <10 | 250 | 250 | <10 | 25 |
| pH 8.2 | 25 | 100 | 50 | 25 | 25 | >500 | >500 | 25 | 25 |
| (B) | | | | | | | | | |
| pH 6.8 | 50 | 250 | 100 | 25 | 100 | 500 | 250 | 50 | 25 |
| pH 8.2 | 50 | 250 | 250 | 100 | 250 | 500 | 250 | 250 | 50 |

TABLE IV

| | Minimum Inhibitory Concentrations for Test Compounds in Yeast/Fungi Species (in ppm) | | | | | | |
|---|---|---|---|---|---|---|---|
| | ORGANISMS | | | | | | |
| COMPOUND | An | Ca | Pc | Sc | Tv | Ap | Fo |
| DOWICIL TM 75 | >500 | >500 | >500 | 500 | >500 | >500 | >500 |
| A | 25 | 100 | <10 | 50 | 50 | 50 | 25 |
| B | 25 | 50 | 10 | 50 | 50 | 25 | 25 |

TABLE II

| Organisms Used in the Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Candida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

What is claimed is:

1. A compound corresponding to the formula

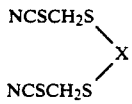

wherein X represents:

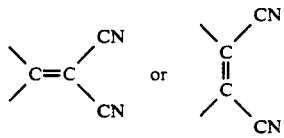

2. The compound of claim 1 wherein X represents:

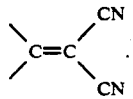

3. The compound of claim 1 wherein X represents:

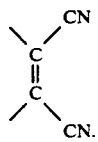

4. An antimicrobial composition comprising an inert diluent and an antimicrobially-effective amount of a compound corresponding to the formula:

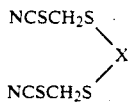

wherein X represents:

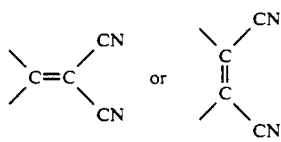

5. The compound of claim 4 wherein X represents:

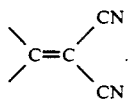

6. The compound of claim 4 wherein X represents:

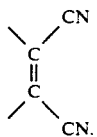

7. The composition of claim 4 wherein the compound is present in the composition in an amount to provide from about 1 part per million to about 5,000 parts per million by weight of the compound to a microbial habitat that is contacted with the composition.

8. A method for inhibiting microorganisms in a microbial habitat comprising contacting said microbial habitat with an antimicrobially-effective amount of a compound corresponding to the formula:

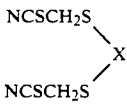

wherein X represents:

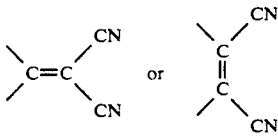

9. The method of claim 8 wherein X represents:

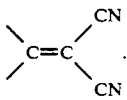

10. The method of claim 8 wherein X represents:

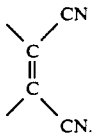

11. The method of claim 8 wherein the compound is present in the composition in an amount to provide from about 1 part per million to about 5,000 parts per million by weight of the compound to the microbial habitat.

* * * * *